United States Patent [19]

Burns et al.

[11] Patent Number: 4,966,592
[45] Date of Patent: Oct. 30, 1990

[54] PROTECTIVE SLEEVE FOR HYPODERMIC NEEDLE

[76] Inventors: Cameron A. Burns; Terry A. Burns, both of 1620 Woolston Ct., Modesto, Calif. 95355

[21] Appl. No.: 347,588

[22] Filed: May 5, 1989

[51] Int. Cl.⁵ .............................................. A61M 5/00
[52] U.S. Cl. ...................................... 604/198; 604/263
[58] Field of Search ............... 604/198, 197, 263, 192

[56] References Cited

U.S. PATENT DOCUMENTS

| | | |
|---|---|---|
| 4,170,993 | 10/1979 | Alvarez . |
| 4,425,120 | 1/1984 | Sampson . |
| 4,643,199 | 2/1987 | Jennings . |
| 4,693,708 | 9/1987 | Wanderer . |
| 4,695,274 | 8/1987 | Fox . |
| 4,702,738 | 10/1987 | Spencer . |
| 4,723,943 | 2/1988 | Spencer . |
| 4,804,371 | 2/1989 | Vaillancourt .................... 604/198 |
| 4,840,619 | 6/1989 | Hughes ............................. 604/198 |

Primary Examiner—Stephen C. Pellegrino
Attorney, Agent, or Firm—Fleit, Jacobson, Cohn, Price, Holman & Stern

[57] ABSTRACT

A hypodermic syringe barrel is provided with an external rotatable and slidable protective sleeve extendable and retractable relative to a needle mounted from the barrel and the sleeve is lightly biased toward the extended position thereof with the needle fully enclosed within the sleeve. The sleeve and barrel are operatively interconnected through utilization of a pin and slot connection defining limits of extension and retraction of the sleeve and the pin and slot connection includes structure whereby angular displacement of the sleeve relative to the barrel may be effected at each limit position of the sleeve for retaining the sleeve in that limit position.

12 Claims, 1 Drawing Sheet

U.S. Patent  Oct. 30, 1990  4,966,592
FIG. 1
FIG. 2
FIG. 3
FIG. 4
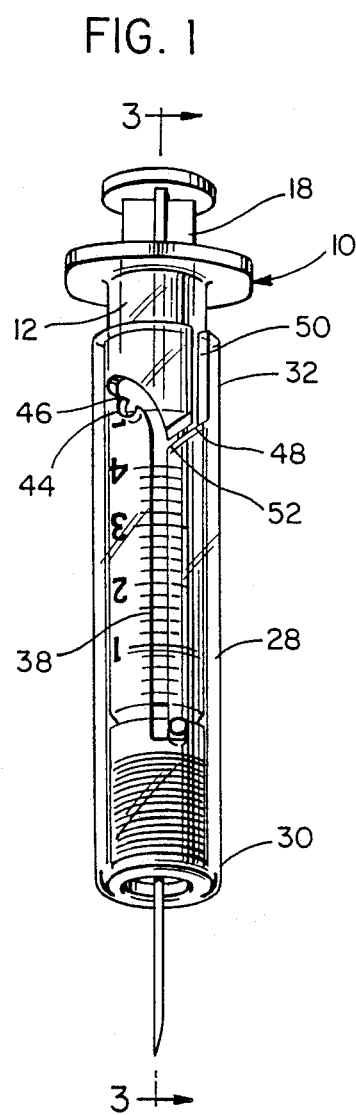
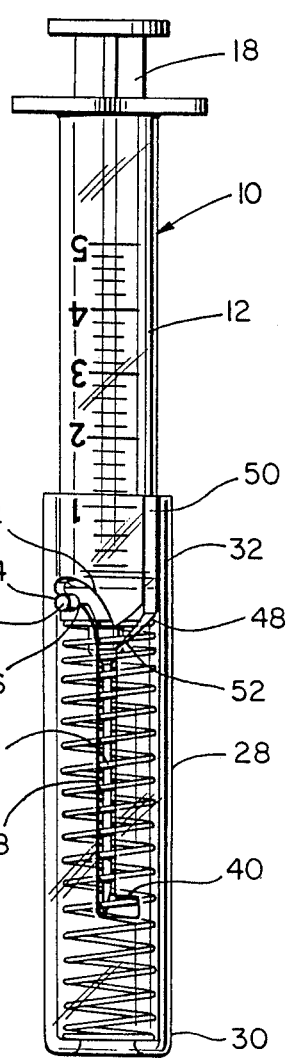
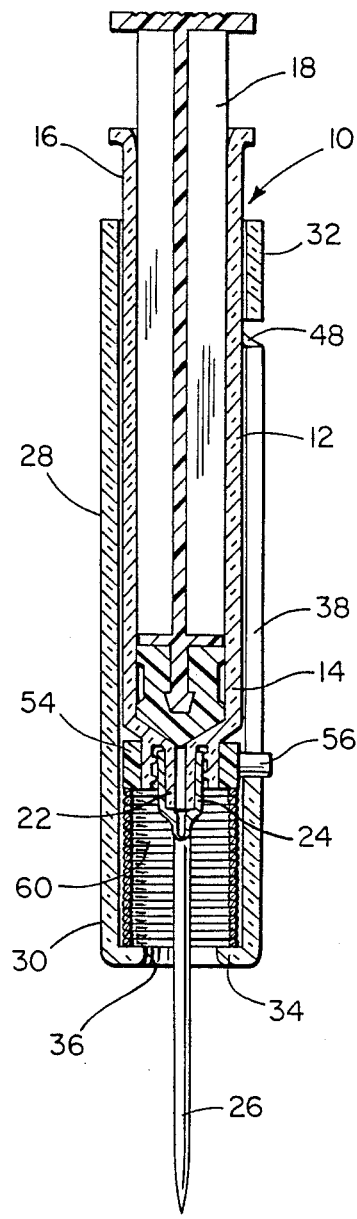
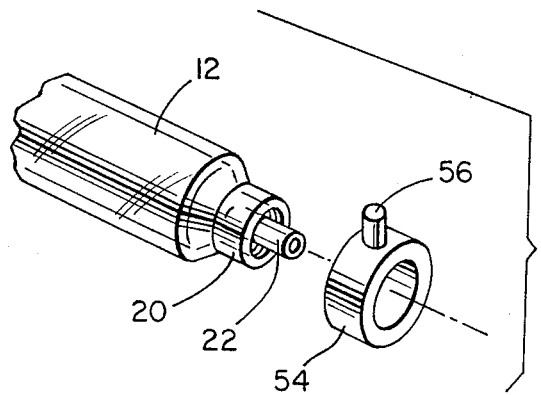

4,966,592

PROTECTIVE SLEEVE FOR HYPODERMIC NEEDLE

BACKGROUND OF THE INVENTION

1. Field of the Invention

This invention relates to a sleeve component guidingly and slidingly telescoped over the needle end of a syringe barrel and shiftable between retracted and extended positions in which an associated syringe barrel supported needle is exposed and covered, respectively. Furthermore, the sleeve is spring biased toward the extended position thereof.

2. Description of Related Art

Various different forms of protective sleeves for hypodermic needles heretofore have been provided such as those disclosed in U.S. Pat. Nos. 4,170,993, 4,425,120, 4,643,199, 4,693,708, 4,702,738 and 4,723,943. However, these previously known forms of protective sleeves do not incorporate the overall combination of structural features included in the instant invention.

SUMMARY OF THE INVENTION

The syringe body and sleeve combination of the instant invention enables the sharpened end of a needle supported from the syringe barrel to be selectively covered and uncovered whenever desired and, in particular, provides an inexpensive manner of maintaining the needle of a used syringe fully covered against accidental contact therewith during and after disposal of the syringe in conventional used syringe receptacles.

The main object of this invention is to provide a protective sleeve for needle equipped syringes and which may be used to maintain the sharpened tip of the needle upon an associated syringe fully covered against accidental contact therewith at all times after withdrawal of the syringe needle from a patient (human or animal).

Another object of this invention is to provide a needle enclosing retractable sleeve for a syringe which may be incorporated into the manufacture of new syringes or added to syringes which have already been manufactured.

Still another object of this invention is to provide a protective sleeve for a syringe and including operational features which enable proper usage of the sleeve even by persons having no prior experience with usage of the sleeve.

Another very important object of this invention is to provide a retractable sleeve for a needle equipped syringe and wherein the sleeve is continuously biased toward the needle tip shielding extended position thereof.

A final object of this invention to be specifically enumerated herein is to provide a retractable needle shielding sleeve for a syringe which will conform to conventional forms of manufacture, be of simple construction and easy to use so as to provide a device that will be economically feasible, long-lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of a typical needle equipped syringe and with the retractable sleeve of the instant invention mounted upon the barrel of the syringe and releasably locked in the retracted position thereof;

FIG. 2 is a side elevational view of the assemblage illustrated in FIG. 1 with the sleeve releasably latched in the extended position thereof;

FIG. 3 is an enlarged vertical sectional view taken substantially upon the plane indicated by section line 3—3 of FIG. 1; and FIG. 4 is a fragmentary perspective view of the needle supporting end of a typical syringe barrel and with a guide pen defining adapter in exploded position relative to the syringe barrl.

DESCRIPTION OF THE PREFERRED EMBODIMENT

Referring now more specifically to the drawings, the numeral 10 generally designates a typical syringe including a barrel 12 having a first needle supporting end 14 and a second finger engageable flange equipped end 16. The syringe 10 also includes a plunger 18 and the first end 14 of the barrel 12 includes an internally threaded sleeve 20 for coupling a catheter to the barrel 12 and a tapered tubular nipple 22 projecting through and endwise outwardly of the sleeve 20 for coupling the hub 24 of a needle 26 to the first end 14 of the barrel 12.

The foregoing comprises a description of a conventional syringe.

In view of the increasing concern of possible contamination of persons handling syringes by having their skin punctured or scratched by contaminated syringe needles, a need exists for structure by which a used needle on a syringe may be totally enclosed within a protective sleeve after possible contamination of the syringe needle.

With reference now more specifically to FIGS. 1, 2 and 3, a protective sleeve referred to in general by the reference numeral 28 is provided including first and second ends 30 and 32. The second end 32 is fully open and the first end 30 includes an annular partial end wall 34 defining a large central opening 36 therein. The sleeve 28 includes an inside diameter, inwardly of the end wall 34, slightly greater than the outside diameter of the barrel 12 and the fully open second end of the sleeve 28 is slidingly telescoped over the first end 14 of the barrel 12.

The sleeve 28 includes a longitudinal control slot 38 formed therein spaced intermediate the opposite ends of the sleeve 28 and the end of the slot 38 adjacent the end wall 34 includes a substantially right angular lateral slot segment 40 while the end of the slot 38 remote from the end wall 34 gradually curves as at 42 in one direction about the sleeve 28. In addition, the curved portion 42 of the slot 38 includes, intermediate its opposite ends, a short longitudinal slot segment 44 extending longitudinally of the sleeve 28 toward the end wall 34. The slot segment 44 includes a reduced width opening 46 immediately adjacent the curved end 42 in which the slot segment 44 opens.

Also, it will be noted from FIGS. 1 and 2 that an entrance slot 48 is provided in the sleeve 28 including a first end 50 opening through the end of the sleeve 28 remote from the end wall 34 and a second end 52 opening into the control slot 38 closely adjacent the curved end portion 42.

With attention now invited more specifically to FIGS. 3 and 4, it may be seen that the sleeve 20 has an adapter sleeve 54 removably and tightly frictionally telescoped thereover and that the adapter sleeve 54 includes a radially outwardly projecting pin 56 slidable through the control slot 38, the slot segment 40, the curved end 42 of the slot 38 and the entrance slot 48, the pin 56 being snap receivable through the reduced width opening 46 leading into the slot segment 44.

Also, it will be noted from FIGS. 2 and 3 of the drawings that a light compression spring 60 is disposed within the first end 30 of the sleeve 28 between the end wall 34 and the opposing axial end face of the adapter sleeve 54. Thus, the compression spring 60 yieldingly biases the sleeve 28 toward the fully extended position thereof defined by the pin 56 being seated in the terminal end of the curved end portion 42 of the slot 38. However, as illustrated in FIG. 2, the barrel 12 may be slightly advanced from the fully retracted position thereof and snap engaged in the slot segment 44. Further, in order to initially engage the sleeve 28 with the barrel 12, the pin 56 is passed through the entrance slot 48 from the first end 50 thereof into the control slot 38.

Of course, if desired, the pin 56 may be formed as an integral component of the barrel 12 and thus not require a separate sleeve such as sleeve 54.

In operation, and assuming that the syringe 10, sleeve 28 and spring 60 are assembled and contained within a sterile envelope when marketed with the sleeve 28 mounted on the barrel 12 in the manner illustrated in FIG. 1, the aforementioned envelope may be opened and the needle 26 may be applied to the tubular nipple 22. Then, if blood is to be drawn from a patient, the syringe 10 may be manipulated such that the tip of the needle 26 properly penetrates a vein from which blood is to be drawn. After the desired quantity of blood has been drawn from the patient, the sleeve 28 may be slightly rotated relative to the barrel 12 such that the pin 54 is displaced from the slot segment 40 into the adjacent end of the control slot 38 whereupon the first end 30 of the sleeve 28 will engage the skin of the patient adjacent the sight penetrated by the needle 26. Thereafter, the syringe 10 may be moved away from the patient's skin in order to withdraw the needle 26 while at the same time the spring 60 lightly yieldingly biases the sleeve 28 toward an extended position such that as the tip of the needle 26 is withdrawn from the skin of the patient, the sleeve 28 will automatically enclose the entire needle 26. Thereafter, if it is desired to express the previously drawn blood from the barrel 12 ahead of the plunger 18, the sleeve 28 may be manually retracted to expose just the tip of the needle 26 and the plunger 18 may be pushed inward to express the previously drawn blood from the syringe 10.

If, on the other hand, the patient is to be injected with serum drawn from a vial, assuming the syringe 10 and sleeve 18 to be positioned as illustrated in FIG. 2, the sterile end wall 34 of the sleeve 12 may be engaged with the mouth of the vial and the barrel 12 may then be rotated relative to the sleeve 28 in order to align the pin with that portion of the control slot 60 between the slot 48 and the terminus of the curved portion 42 of the slot 38. Then, the syringe 10 may be pushed forward relative to the sleeve such that the tip of the needle will pierce the center of the diaphragm across the neck of the vial from which fluid is to be drawn. Fuild may then be drawn from the vial in the usual manner and as the syringe 10 is pulled from the vial the sleeve 28 will automatically be returned to the fully extended position thereof enclosing the entire neeld 26. Thereafter, just before the serum within the syringe 10 is to be injected into a patient, the sleeve 28 may be partially retracted relative to the needle 26 sufficient to expose only that much of the needle as required to effect the desired serum injection into a patient. At this time, the sleeve 28 may be released for engagement of the end wall 34 with the skin of the patient about the injection site and the plunger 18 may be pushed forward to inject the serum from the syringe into the patient. Of course, as the syringe 10 is withdrawn from the patient after the injection process has been completed, the sleeve 28 returns to a fully extended position again fully enclosing the needle 26 therein.

At this point, the sleeve 28 may be rotated relative to the barrel 12 in order to engage the pin 56 in the slot segment 40 and the syringe 10 may be discarded in the usual receptacle therefor. In this manner, even should a person place his or her hand into a receptacle for discarded syringes, the needles thereof will be fully enclosed within the protective sleeves therefor.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An elongated syringe barrel component including needle mounting means at one end and a needle mounted from said needle mounting means and projecting endwise outwardly of said one end, a protective sleeve component having first and second ends, said sleeve component being slidingly telescoped over said one end of said barrel component and rotatable relative thereto with a first end of said sleeve component shiftable between extended and retracted limit positions relative to said one end, said sleeve component, when in said retracted position, projecting a predetermined extend outwardly of said one nd inwardly of the outer extremity of said needle and when in said extended position extending outward of said outer extremity, biasing means operatively connected between said barrel and sleeve components lightly yieldingly biasing said sleeve component toward said extended position, said barrel and sleeve component including coacting pin and slot connection means establishing said limit positions and effecting rotational oscillation between said barrel and sleeve components as said sleeve component completes and initiates its movement toward and away from, respectively, said retracted position, said pin and slot connection means including a longitudinal control slot formed in one of said components and a pin carried by the other component slidingly and guidingly received in said control slot, said control slot including first and second closed end portions defining said extended and retracted limit positions, respectively, said first end portion extending laterally in one direction partially about said one component and said second end portion incorporating a lateral slot segment extending partially about said one component in which said pin may be received from said control slot second end portion and retained against the biasing action of said biasing means, said first end portion, including a slot segment extending a short distance longitudinally of said one component toward said other slot end portion and in which said pin is receivable, said one component also including an entrance slot formed therein including one end opening into said control slot intermediate the closed ends of said control slot end portions and a second end opening endwise outwardly of said one component adjacent the end thereof remote from said lateral slot segment.

2. The syringe barrel and sleeve components of claim 1 wherein said slot segment extending longitudinally of said one component includes reduced width zone thereof adjacent the terminus of said laterally extending first end portion through which said pin is snap receivable.

3. The barrel and sleeve components of claim 1 wherein said one component comprises said sleeve component.

4. The syringe barrel and sleeve components of claim 1 wherein said first end of said sleeve component includes an annular partial end wall, said biasing means comprising a coiled compression spring interposed between the inner surface of said annular partial end wall and said one end of said barrel and through which said needle is loosely received.

5. The barrel and sleeve components of claim 1 wherein said one component comprises said sleeve component, said one end of said barrel component including a reduced diameter endwise outwardly projecting sleeve in which the hub end of said needle is secured, said pin being carried by an accessory sleeve telescoped over and tightly fitted upon said reduced diameter sleeve.

6. The syringe and sleeve components of claim 5 wherein said first end of said sleeve component includes an annular partial end wall, said biasing means comprising a coiled compression spring interposed between the inner surface of said annular partial end wall and said one end of said barrel and through which said needle is loosely received.

7. The barrel and sleeve components of claim 6 wherein said one component comprises said sleeve component.

8. The barrel and sleeve components of claim 7 wherein said slot segment extending longitudinally of said one component includes a reduced width zone thereof adjacent the terminus of said laterally extending first end portion through which said pin is snap receivable.

9. An elongated syringe barrel component including needle mounting means at one end and a needle mounted from said needle mounting means and projecting endwise outwardly of said one end, a protective sleeve component having first and second ends, said sleeve component being slidingly telescoped over said one end of said barrel component and rotatable relative thereto with a first end of said sleeve component shiftable between extended and retracted limit position relative to said one end, said sleeve component, when in said one retracted position, projecting a predetermined extent outward of said end inward of the outer extremity of said needle and when in said extended position extending outward of said outer extremity, said barrel and sleeve components including coacting pin and slot connection means establishing said limit positions, said pin and slot connection means including a longitudinal control slot formed in said sleeve and a pin carried by said barrel component, said one end of said barrel component including a reduced diameter sleeve projecting endwise outwardly thereof within which the hub of said needle is mounted, an accessory sleeve snugly and frictionally removably telescoped over and retained on said reduced diameter sleeve, said pin being carried by said accessory sleeve.

10. The barrel and sleeve components of claim 9 including biasing means operatively connected between said barrel and sleeve components lightly yieldingly biasing said sleeve component toward said extended position.

11. The barrel and sleeve components of claim 10 wherein said first end of said sleeve component includes an annular partial end wall, said biasing means comprising a coiled compression spring interposed between the inner surface of said annular partial end wall and said one end of said barrel and through which said needle is loosely received.

12. An elongated syringe barrel component including needle mounting means at one end and a needle mounted from said needle mounting means and projecting endwise outwardly of said one end, a protective sleeve component having first end second ends, said sleeve component being slidingly telescoped over said one end of said barrel component and rotatable relative thereto with a first end of said sleeve component shiftable between extended and retracted limit positions relative to said one end, said sleeve component, when in said retracted position, projecting a predetermined extent outwardly of said one end inwardly of the outer extremity of said needle and when in said extended position extending outward of said outer extremity, biasing means operatively connected between said barrel and sleeve components lightly yieldingly biasing said sleeve component toward said extended position, said barrel and sleeve component including connection means establishing said limit positions and effecting rotational oscillation between said barrel and sleeve components as said sleeve component completes and initiates its movement toward and away from, respectively, said retracted position, said connection means also including means preventing movement of said sleeve from said extended position toward said retracted position, upon opposite directional forces being applied longitudinally to said sleeve an barrel components sufficient to overcome the biasing action of said biasing means, independent of also applying opposing rotational forces to said components to effect reverse relative rotational displacement therebetween.

* * * * *